United States Patent [19]

Almog et al.

[11] Patent Number: 4,839,294
[45] Date of Patent: Jun. 13, 1989

[54] COLORIMETRIC ASSAY AND METHODS FOR USING SAME

[75] Inventors: Rami Almog, Albany; Carol Anderson-Samsonoff, Glenmont; Donald S. Berns, Alabany, all of N.Y.

[73] Assignee: Health Research Inc., Albany, N.Y.

[21] Appl. No.: 88,627

[22] Filed: Aug. 24, 1987

[51] Int. Cl.[4] .............................................. G01N 33/92
[52] U.S. Cl. ......................................... 436/71; 436/13; 436/63
[58] Field of Search ....................... 435/11, 13, 18, 19; 436/13, 71, 63; 422/55–58; 424/2; 252/408.1

[56] References Cited

U.S. PATENT DOCUMENTS

4,195,126  3/1980  Hall ........................................ 436/71
4,369,250  1/1983  Gindler ................................... 436/13

Primary Examiner—Barry S. Richman
Assistant Examiner—T. J. Wallen
Attorney, Agent, or Firm—Curtis, Morris & Safford

[57] ABSTRACT

This invention relates to an assay useful for the evaluation of the lipid content of a biological fluid and its content in aqueous dispersion. The assay of the invention utilizes a dye-detergent complex which when solubilized by an aqueous dispersion of lipid-containing fluid sample, exhibits a characteristic color. The invention also provides for the use of the assay in the evaluation of the lipid content of a fluid, particularly amniotic fluid, which evaluation is useful for the prediction of Respiratory Distress Syndrome in newborns.

11 Claims, 3 Drawing Sheets

COLORIMETRIC ASSAY AND METHODS FOR USING SAME

FIELD OF THE INVENTION

The field of this invention is the evaluation of the presence of certain lipids in biological fluids. More specifically, the invention relates to a novel colorimetric assay useful in the prediction of Respiratory Distress Syndrome in newborns, which syndrome is associated with inadequate fetal pulmonary surfactant function. The invention provides a rapid and specific assessment of the status of fetal pulmonary surfactant by assaying for the presence of various lipids in amniotic fluid. The lipid content of the amniotic fluid provides a profile of the lipid content of the surfactant, and consequently an evaluation of fetal pulmonary maturity.

BACKGROUND OF THE INVENTION

Respiratory Distress Syndrome (RDS) is a progressive respiratory failure in newborns caused by inadequate surfactant function. Approximately 26,000 infants died of RDS during the years 1975 to 1978 and many others suffered significant short- and long-term morbidity as a result of the disease and its therapy annually. The average hospital costs are about 2.5 times higher for premature infants with RDS than without. Thus, there are both medical and economic reasons for exploring new possibilities for simple and reliable prediction of RDS, as well as effective and safe therapies for the disease.

The need to assess in particular the status of the surfactant, a complex mixture predominantly of phospholipids with smaller amounts of protein, in pregnancies in which fetal well-being is jeopardized by maternal diabetes mellitus, toxemia, induced labor or delivery by Caesarian section is commonly recognized. There are no known clinically applicable methods of directly quantitating surfactant in the alveoli and airways, but fortunately substitute methods are available. Fluid continuously moves out of the lungs before birth and carries surfactant into the amniotic fluid. Surfactant components can be measured in the fluid, and have a good correlation with pulmonary surfactant.

Currently, the most accepted clinical test has been the amniotic fluid lecithin/sphingomyelin (L/S) ratio. The L/S assay uses centrifugation of the fluid to remove cell debris, lipid extraction with chloroform-methanol mixture, removal of "non-surfactant" lecithin by cold acetone precipitation and separation of phospholipids by one or two dimensional thin layer chromatographic procedures. The ratio of L/S is determined by either densiometry of the chromatogram to measure the intensity of each spot; by planimetry to estimate their area; or by phosphorus analysis, to determine the amount of each lipid.

Helena L/S ratio kit (Helena Fetal-Tek 200) marketed by Helena Laboratories, 1530 Lindbergh Dr. P.O. Box 752, Beaumont, Tex. 77704, is based on this technique. A L/S ratio of 2.0 which represents a mature value is basically reliable when performed according to a strictly prescribed procedure. However, technical expertise and the strictest quality control measures are necessary to successfully perform the time consuming procedure and correctly interpret the data. In addition, a number of abnormal conditions encountered in pregnancy such as diabetes mellitus, Rh isoimmunization, maternal hypertension, premature deliveries or membrane rupture, as well as contamination of the amniotic fluid with blood or meconium, are known to cause altered lecithin values which may give a false indication of lung maturity in the fetus, thus resulting in large number of false predictions. There are several modifications of this technique which use some form of lipid extraction followed by separation on thin layer chromatography and then lipid determination. All of them have limitations similar to those attributed to the L/S method.

Fluorescence polarization measurement of amniotic fluid is also used for determination of fetal lung maturity. Fluorescence polarization is a measure of the microviscosity of the whole lipid assembly of amniotic fluid and claimed to reflect an overall property, not yet fully understood, of the total lipid mixture present in the fluid. Fluorescence polarization values correlate with changes in L/S ratio but also suffer from blood contamination in addition to intrinsic problems associated with fluorescence measurements. Finally, the fluorescence polarization method requires very expensive instrumentation.

There are some rapid assays such as the shake test and the absorbance measurement at 650 nm which demonstrate some correlation with L/S ratio. The shake test or the foam stability index is based on the presence of surfactant in amniotic fluid to form a stable foam in the presence of ethanol. These assays are straightforward and inexpensive techniques. However, their predictive values are relatively low and are affected by any contamination in the fluid. In addition, they do not measure specific elements of surfactant in the fluid. Therefore, they are mostly used as screening assays and in combination with other assays.

Recently, it has been recognized that two specific phospholipids, phosphatylglycerol (PG) and phosphatidylinositol (PI), are very important to the biological process of lung maturation and that their determination in amniotic fluid aids in prediction of RDS. It is believed that PG analysis predicts the level of maturity more accurately than the L/S test. The presence of PG, even with an L/S ratio indicating lung immaturity predicts that the fetus will be free of RDS. PG and PI are present in blood in very small amounts. Therefore, assays detecting their presence in amniotic fluid will not suffer from contamination with blood.

In most normal pregnancies, PI increases after 30 weeks of gestation and peaks at 36-37 weeks. PG increases after 35 weeks and continues to increase beyond term. Initially, only Thin Layer Chromatography (TLC) methods were available for PG analysis. As in the case regarding TLC analysis of L/S ratios, the technique is subject to many variables, is difficult to perform and is very time consuming. In addition, PG determination requires additional steps beyond those needed for L/S ratios.

Because of these problems, several other assays for PG were proposed. Hana Biologics, Inc., 626 Bancroft Way, Berkley, Calif. 94710, has commercialized a biochemical immunologic agglutination test for determining the presence of PG (Amniostat-FLM). The assay is said to be specific, sensitive and fast. The results of the tests are not affected by blood or meconium contamination of fluid samples. However, since the assay is expressed as a negative, positive or strong positive for the presence of PG, it can be used only as a screening test, or as one in a series of tests performed to obtain a more thorough assessment of fetal lung maturity. A major limitation of this procedure is that it relies on biological reagents which are labile and require careful storage conditions. In addition, the agglutination reaction is temperature dependent and not all specimens will produce agglutination patterns identical to the equivalent control reaction. Special care has to be taken when looking for "clearing in the background" of the agglutination reaction, otherwise a false positive interpretation may be obtained. Recently, a new enzymatic method for quantitating PG in amniotic fluid has been offered by ISOLAB Inc., Akron, Ohio.

There is no commercial procedure, however, which incorporates the determination of PI for evaluating lung maturation. There is also a growing number of investigators and hospitals who assay for more than one phospholipid when assessing fetal pulmonary maturity. Thus the sum of all surface active phospholipids, a combination of the L/S ratio and PG determination and the total phospholipid concentration in the lamellar body fraction of amniotic fluid are being used.

In summary, the current methods used in prediction of lung maturity suffer from one or more of the following disadvantages: they require technical expertise and expensive instrumentation; they are time-consuming; they lack specificity and sensitivity and use unstable biological reagents, and/or they are at best only semiquantitative. All this is reflected in inconsistent data and large expenses per test.

Therefore, a great need exists for a rapid, simple, inexpensive, and accurate test for the evaluation of the lipid content of biological fluids, for example, the evaluation of amniotic fluid, which information is used in the prediction of fetal pulmonary maturity.

OBJECTS OF THE INVENTION

It is an object of the invention to provide a rapid and specific assay for the quantitative evaluation of the presence of lipids in biological fluids and in aqueous dispersions which are used as models for biological membranes.

It is another object of the invention to provide a method of quantitatively evaluating the presence of lipids in biological fluids and in aqueous dispersions by means of a rapid and specific assay.

It is also an object of the invention to provide a rapid, simple, inexpensive and accurate assay useful for the prediction of Respiratory Distress Syndrome in newborns.

It is still another object of the invention to provide a method of predicting Respiratory Distress Syndrome by means of a rapid, simple, inexpensive and accurate assay useful for the prediction of Respiratory Distress Syndrome in newborns.

It is a further object of the invention to provide a rapid and specific assay which can assess the status of fetal pulmonary surfactant, the status of which can be used to predict Respiratory Distress Syndrome.

It is yet another object of the invention to provide a method of predicting Respiratory Distress Syndrome by means of a rapid and specific assay which can assess the status of fetal pulmonary surfactant, the status of which is useful in the prediction of Respiratory Distress Syndrome.

It is also an object of the invention to provide a rapid and specific assay which can evaluate the status of fetal pulmonary surfactant by means of determining the presence of various lipids in amniotic fluid.

It is still another object of the invention to provide a rapid and specific assay which provides an evaluation of the lipid content of the fetal pulmonary surfactant and consequently of fetal pulmonary maturity, through an evaluation of amniotic fluid.

It is also an object of the invention to provide an assay useful for the prediction of fetal lung maturity, which assay utilizes reagents which are stable at room temperature and which have long shelf lives.

It is yet another object of this invention to provide an assay useful for the prediction of fetal lung maturity, results of which assay are not altered by the presence of contaminants in the sample tested.

It is also an object of the invention to provide an assay which allows for the determination of the lung maturity of the fetus at an earlier stage in fetal development.

It is a further object of the invention to provide an assay useful for the prediction of fetal lung maturity, which assay provides for an assessment of charged phospholipids such as PG and PI, uncharged phospholipids such as phosphatidylcholine (PC), and total phospholipid concentrations.

It is still another object of the invention to provide an assay useful for the prediction of fetal lung maturity, which allows for quantitative, rather than qualitative, assessment of the relevant phospholipids present in amniotic fluid.

These and other object are met by the present invention.

STATEMENT AND ADVANTAGES OF THE INVENTION

The present invention is directed, inter alia, to a rapid and specific assay useful for the quantitative evaluation of the presence of lipids in biological fluids and aqueous dispersions of phospholipids. More specifically, the assay is useful in the prediction of Respiratory Distress Syndrome in newborns through an evaluation of the anionic, zwitterionic and total phospholipids in amniotic fluid. The inventive assay utilizes a stable reagent, for example, a complex formed between the common dye Coomassie Brilliant Blue (CBB) and cetyltrimethylammonium bromide in order to determine the presence of various lipids in amniotic fluid. This information in turn provides an evaluation of the lipid content of fetal pulmonary surfactant, which in turn is used for determining fetal lung maturity and predicting the likelihood of RDS in the newborn.

The assay procedure is based on the phenomenon that dyes can associate with various detergents. At about equal molar ratios of dye to opposite-charged detergent, there is a drastic lowering of dye absorbance due to formation of a water-insoluble complex. We have observed that the complex formed by association between a dye such as CBB, for example, and a detergent such as, for example, cetyltrimethyammonium bromide can be solubilized by lipid suspensions, resulting in a characteristic blue-colored solution. This property of the lipids may be used in order to determine their concentrations.

A negatively charged dye such as CBB is associated with the positively charged detergent to form a complex which is isolated by centrifugation, filtration or adsorbed onto a glass bead. The complex is redissolved by association with the phospholipid to be determined. The phospholipid concentration is then determined by measuring the changes in the light absorbance of the resulting solution. Increased specificity is achieved by distribution of the specific associated phospholipid complex between chloroform and an aqueous medium.

The inventive assay can be used for a rapid determination of the concentrations of anionic, zwitterionic and total phospholipids in the fluid tested. When specific determination of certain lipids, for example, PG or PI are needed, these lipids can be separated by chromatography, using for example micro-columns such as Waters Associates' SEP-PAK cartriges, and then may be determined by the assay in individual fractions.

The assay according to the invention is a rapid, simple, inexpensive and accurate assay which can assess the lipid content of fluids. The assay is particularly advantageous when used to evaluate the lipid content of amniotic fluid. This evaluation provides, in turn, information on the lipid content of fetal pulmonary surfactant and consequently of fetal pulmonary maturity.

The assay utilizes reagents which are stable at room temperature and which have long shelf lives and avoids the use of unstable biological reagents. This assay also provides a measurement of lipid content of fluids, the results of which assay are not altered significantly by the presence of contaminants, for example, blood or meconium, in the sample tested.

The assay also provides for an assessment of the charged and uncharged phospholipid content, their ratio and also a determination of the presence of individual lipids.

The invention therefore provides for a simple, inexpensive and specific assay which allows for the quantitative, rather than qualitative assessment of relevant lipids present in biological fluids, such as amniotic fluid.

DESCRIPTION OF CERTAIN PREFERRED EMBODIMENTS

The provision of a rapid and specific colorimetric assay which can be used, for example, for the prediction of Respiratory Distress Syndrome, is dependent upon the recognition of the phenomenon that dyes can associate with various detergents to form a complex, which complex can be solubilized by lipid suspensions to yield a characteristically colored solution. This property of lipids and their propensity for association with various water insoluble dye-detergent complexes, causing their dissolution into water, is utilized in the assay in order to determine the concentration of these lipids present in a fluid such as amniotic fluid. Evaluation of amniotic fluid lipid content provides an evaluation of the status of the pulmonary surfactant of the fetus. The dye used is such that when it associates with a detergent, it forms a water insoluble product which is solubilized by phospholipids to result in a characteristically colored solution. A particularly advantageous feature of the invention is that the dye and detergent used to form the dye-detergent complex are stable, common and inexpensive reagents, with a long shelf life.

In accordance with one embodiment of the invention, a dye which may be used is the common dye Coomassie Brilliant Blue (CBB). When a dye such as CBB is associated with a certain positively charged detergent, for example, cetyltrimethylammoniumbromide, at about equal molar ratios of dye to opposite-charged detergent, there is a drastic lowering of dye absorbance due to formation of a water-insoluble complex. The complex formed by association between CBB and the dye can be solubilized by lipid suspensions to yield a blue-colored solution, and this property of lipids is used to determine their concentration. The negatively charged CBB is associated with a positively charged detergent to form a complex which is isolated by centrifugation, filtration, or adsorbed onto a glass bead. The complex is then redissolved by association with the phospholipid to be determined. The phospholipid concentration is then determined by measuring the changes in the light absorbance of the resulting solution. Increased specificity is achieved b distribution of the specific associated phospholipid complex between chloroform and an aqueous medium. The inventive assay is particularly helpful for the measurement of phospholipid content in amniotic fluid.

In yet another aspect, the invention provides for a method for quantitatively evaluating the presence of lipids in a fluid sample, and for predicting Respiratory Distress Syndrome using the inventive assay.

Further objects of the invention, together with additional features contributing thereto and accruing therewith, will be apparent from the following examples of the invention.

BRIEF DESCRIPTION OF THE DRAWINGS

FIG. 2. Glass bead assay for phospholipid liposomes. Ten beads according to the invention were shaken in 2 ml of liposomes of various phospholipid concentrations at 35° C. for 30 min. The absorbance at 618 nm is shown (−) PG(●), PI(▲), and PC(■). To this solution, 3.0 ml of chloroform and 2.0 ml of methanol were added and vortexed. The absorbance at 618 nm of the aqueous phase is shown (—) PG (○), PI(Δ), and PC(□). No correction for change in volume of the aqueous phase after extraction was applied.

FIG. 5. The correlation between the rapid assay (as in FIGS. 2 and 3) and L/S ratios. A. Absorbance at 618 nm prior to extraction of the blue solution obtained by application of the inventive assay to amniotic fluids. B. The absorbance at 618 nm of the aqueous phase after organic solvent extraction. C. The absorbance at 618 nm of he organic phase after extraction.

EXAMPLE I

A. Materials

L-phosphatidyl-DL- glycerol (PG) from egg yolk lecithin. L-phosphatidylinositol (PI) from soybean, and L-phosphatidylcholine (PC) type VII-E from egg yolk were purchased from Sigma Chemical Company and were 98–99% analytically pure. Cetyltrimethylammoniumbromide (CTAB) was obtained from Eastman Organic Chemical Company and Coomassie Brilliant Blue G-250 (CBB) from Polysciences, Inc. Nitrocellulose filters (0.22-8.0 μm pore size) were from Millipore or Schleicher and Schuell. Polished pyrex glass beads were from Corning.

B. Methods

1. Preparation of liposomes (aqueous dispersion of lipid). Lipids in organic solvents were evaporated to dryness under nitrogen, weighed, and resuspended in distilled water to a concentration of 2 mg/ml in a tightly stoppered tube flushed with nitrogen, and sonicated 90 min at 30°-35° C. Insoluble material was removed by centrifugation at 1500×g for 20 min. Liposomes stored at 4° C. under nitrogen were used within a week of preparation.

2. Preparation of the dye-detergent complex. Aqueous solutions containing a final concentration of $8\times10^{-5}$M detergent Cetyltrimethylammonium bromide (CTAB) and $5\times10^{-5}$M Coomassie Brilliant Blue (CBB) were vortexed briefly and incubated at room temperature for 20 min. The resultant water insoluble dye-detergent complex was collected by several methods.

a. Two-ml aliquots of the dye-detergent mixture were placed in centrifuge tubes, and centrifuged at 12,000×g for 10 min. The pelleted complex was used directly.

b. Five-ml aliquots of the dye-detergent mixture were filtered through a 13 mm diameter nitrocellulose filter in a Millipore Swinnex holder attached to a 5 ml syringe. The blue precipitate on the filter was air dried at room temperature before use.

c. The precipitated complex from 424 ml of dye-detergent mixture was collected by centrifugation at 10,000×g for 20 min, and dissolved in 4 ml methanol. Glass beads (32 g, 3 mm) were added and dried, with occasional stirring, under a stream of nitrogen. As the solvent was evaporated, the complex was adsorbed to the beads and the complex-coated beads were used in the method described in 4 below.

3. Extraction of lipids from amniotic fluid. Amniotic fluids were centrifuged 900×g 10 min. Lipids were extracted from 2 ml aliquots with 2:1 volumes of chloroform to methanol. The chloroform phase was dried under a stream of nitrogen, resuspended in 2 ml of 0.025 phosphate, pH 7.0, and sonicated in a bath sonicator at room temperature for 15 min to form amniotic fluid-lipid liposomes. This period may be shortened by using a sonication probe for 1 to 2 min.

4. Method for detection of lipids. The complex adsorbed onto beads or deposited on a nitrocellulose filter were placed in 16×125 mm glass tubes containing 2.0 ml or 1.0 ml respectively of synthetic phospholipid liposomes or lipids extracted from amniotic fluid. Assay tubes were then incubated in a shaking water bath at 35° C. for 30 min. The beads were removed and 3 ml of chloroform and 2 ml methanol were added. The mixture was vortexed for 5 sec and centrifuged at 12,000×g for 10 min. The dye-detergent-lipid complex partitioned between the organic and aqueous phases. The concentrations of the charged lipids in the aqueous phase and the uncharged lipids in the organic phase were determined by measuring the absorbance at 610 nm or at 618 nm or at 618 nm with a Perkin-Elmer 320 spectrophotometer.

When the complex was used directly in a centrifuge tube, a 1.0 ml sample of phospholipid liposomes was added to the precipitate and the mixture was incubated with shaking (150 rpms) at 35° C. for 30 min. The absorbance of the resultant solution was measured at 618 nm.

Results:

A water insoluble dye complex between CBB and CTAB (1:1) was formed as in Methods (B.2) The complex, when collected by the various means described herein, was redissolved by phospholipid liposomes suspension in water. Charged phospholipids have shown a discriminating ability to solubilized the dye-detergent complex when the complex was deposited on nitrocellulose filter. Table I shows that PG solubilize the complex to a larger extent than PC, when procedure 2.a. was followed. The sensitivity and specificity of the response toward PG (or charged phospholipids) were tested using other methods of complex collection such as filtration and adsorption on glass beads.

Figure 1:
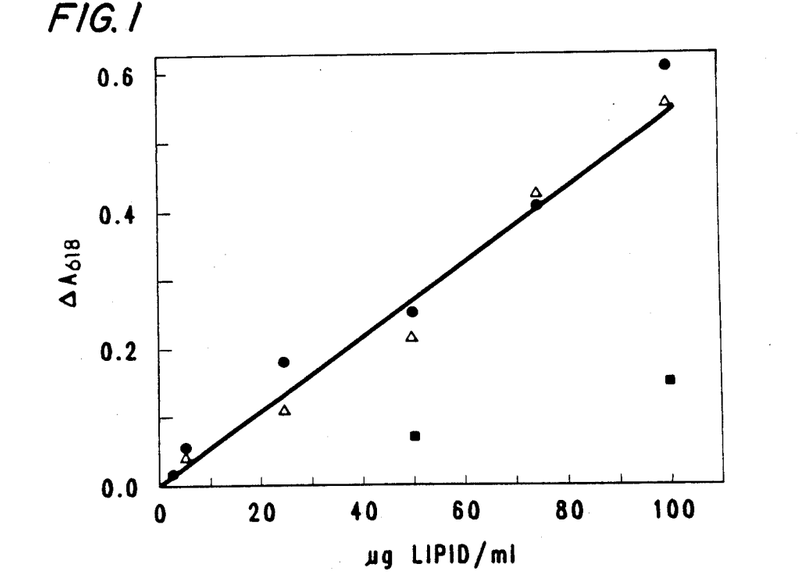
FIG. 1. Standard response curve for phospholipid liposomes (water dispersions of phospholipids) using the nitrocellulose filter method. A filter with deposited dye-detergent complex was shaken in 1 ml of liposomes at 35° C. for 30 min. Absorbances at 618 nm as a function of phospholipid concentration are given, PG(●), PI(Δ) and PC(■).

Standard curves of phospholipids were constructed using dye-detergent complex deposited on a nitrocellulose filter. The complex was collected on a Millipore filter having an 8 μm pore size (procedure B.2.b.). FIG. 1 shows a response curve for 10-100 μg/ml of PG, PI and for several PC concentrations. This method allows for the detection of PG or PI with some interference from PC. Sensitivity relatively to procedure B.2.a. is reduced, however, and in fact the method lacks sensitivity below 10 μg/ml of charged lipids.

Figure 2:
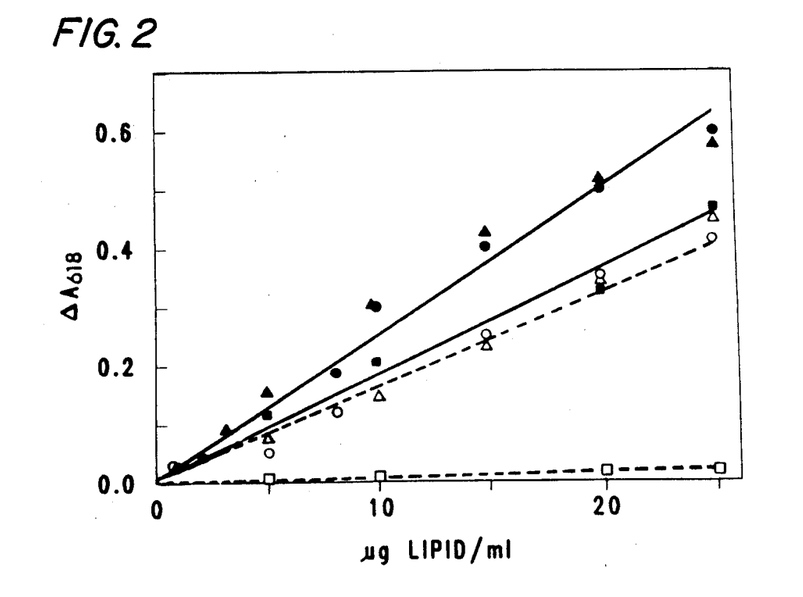

Increased sensitivity was needed in order to detect small amounts (10 μg/ml) of charged phospholipids found in amniotic fluid. This was achieved by adsorbing the dye-detergent complex onto glass beads, as described in B.2.c and B.4., thus increasing the surface area contact between the complex and the phospholipid preparation. As little as 2 μg/ml of phospholipid can be detected with this method (FIG. 2 and Tables II and III). Using the glass beads method the response from PC was also improved.

Figure 3:
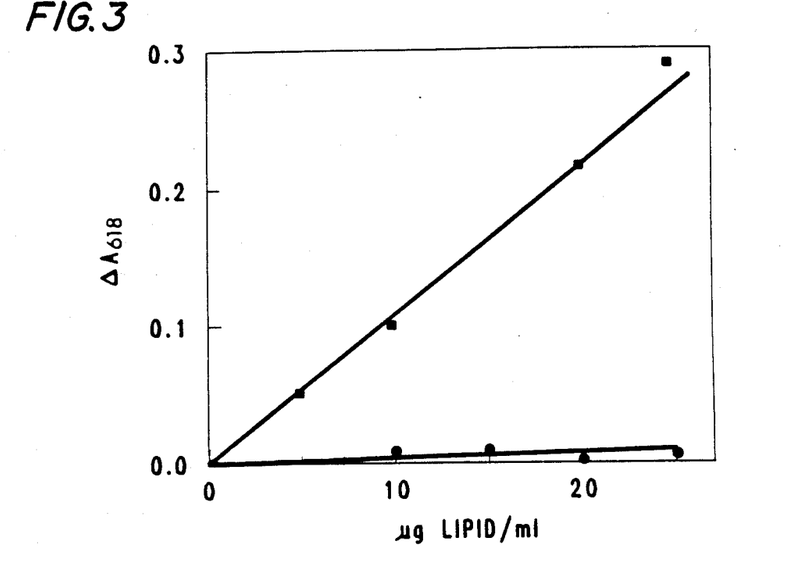
FIG. 3. Organic phase of extracted assay. Assay and chloroform-methanol extraction was performed as in FIG. 2. Absorbance changes at 618 nm of the organic phase as a function of phospholipid concentration are shown, PG (●), PC (■). PI behaved as PG.

As shown in FIG. 2, the increase in absorbance at 618 nm, indicating resolubilization of the complex in solution, was linear with increasing amount of the charged lipids PG, PI and PS. Values shown were obtained using ten complex-coated beads per 2 ml of liposomes. Values obtained using water rather than liposomes were subtracted as background and all data were analyzed by linear regression. The capability of the assay to detect anionic lipids without interferences from zwitterionic lipids was dramatically improved by subjecting the dye-detergent complex, solubilized by the phospholipid, to chloroform-methanol extraction. As shown in Table II the chloroform-methanol extraction increases significantly the specificity of the test by extracting the dye associated with zwitterionic lipids to the chloroform phase. The dye solubilized by charged lipids (PG, PI), as measured by absorbance at 618 nm, was recovered entirely in the aqueous phase. The standard curves were the same for all the charged lipids tested (FIG. 2). The PC-solubilized dye which was found in the chloroform phase showed a similar linear increase in absorbance at 618 nm as a function of lipid concentration (FIG. 3). The absorbance in the aqueous phase due to PC was very small (FIG. 2). Sphingomyelin(S) is a relatively poor solvent for the dye-detergent complex and therefore its contribution to the absorbance in the organic phase would be relatively small (Table II). Phosphatidylethanolamine (PE) is also extracted into the organic phase (Table II).

It should be noted that the extraction step (1 volume aqueous sample with 1.5 volume chloroform and 1 volume methanol) almost doubles the original volume of the sample since most of the added methanol is miscible with the aqueous phase. The absorbance at 618 nm of the aqueous phase after extraction, would therefore be expected to decrease by a factor of two. The decrease was actually 1.5 because the extinction coefficient of CBB is larger in 1:1 v/v methanol:$H_2O$ than in water (Table II). The decrease in absorbance does not affect the sensitivity of the method, however. When higher sensitivity is desired, the methanol can be evaporated under nitrogen or alternatively the aqueous phase is made 1% saturated with ammonium sulfate, 1.0 ml of chloroform is added and the mixture is vortexed for 25 sec. The dye entity is transferred completely into the organic phase under this treatment.

The capability of the method to determine PG in the presence of PC, was assessed by applying the inventive assay to liposomes of a mixture of PC and PG (Table II and III). The assays were performed as described above. Ratios of PC to PG, similar to that found in amniotic fluid, were used. The aqueous PG and the organic PC values in the mixture were essentially those of each lipid alone, demonstrating that small amounts of PG can be detected in the presence of larger amounts of PC.

Figure 4:
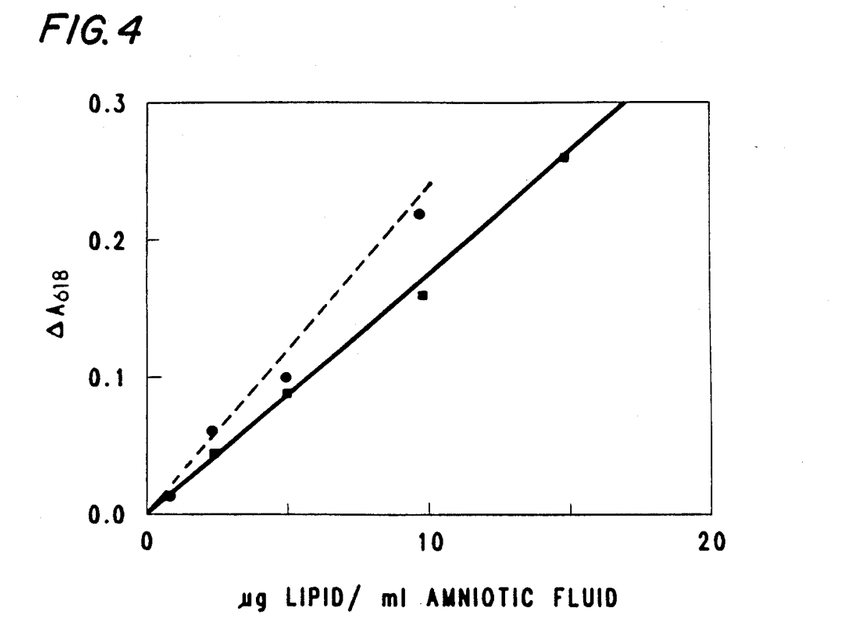
FIG. 4. Assay for exogenous phospholipid in amniotic fluid. Increases in absorbance at 618 nm as a function of lipid added to pooled amniotic fluid. Assays were performed as described in FIGS. 2,3. PG and PI (●) were recovered in the aqueous phase (—) and PC (■) in the chloroform phase (—).

The applicability of the test to amniotic fluid was determined by assaying pooled amniotic samples enriched with particular exogenous commercial lipids. The application of the inventive assay directly to enriched amniotic fluid could not consistently detect up to 10 μg/ml PG. Therefore, the lipid component was extracted from the fluid by a chloroform-methanol mixture before assaying. FIG. 4 illustrates the recovery of PG in the presence of extracted phospholipids from pooled amniotic fluid. The pooled fluids were samples having L/S ratios greater than 2 reflecting lung maturation. Data are presented as changes in $A_{618}$ values from which control values of pooled amniotic fluid without added lipid were subtracted. The response is linear with increasing PG and capable of detecting as little as 2 μg/ml. Added PC can be detected by increased absorbance in the chloroform phase (FIG. 4).

Table III shows that a mixture of exogenous lipids added to an amniotic fluid pool results in an absorbance increase which is an additive response of the individual phospholipids. Again, the PG is found in the aqueous phase and the PC in the organic phase. The ratio of lipids used was meant to reflect amniotic fluid with an L/S ratio greater than two. Table IV also shows that the large ratio of PC to PG does not prevent the detection of PG and that the inventive method can assay small changes in PG concentration in amniotic fluid, thus providing a sensitive method for determination of lung maturity. The absorbance values of the aqueous and organic phases can be converted to quantitative concentrations by using appropriate standard curves utilizing purified phospholipids. The averaged values for several pooled amniotic samples (without addition of exogenous lipids) were 0.11 for the aqueous phase and 0.42 for the organic phase. These values correspond (from FIGS. 2 and 3) to 10 μg/ml charged lipids and about 39 μg/ml uncharged lipids, which are within the range reported using other methods.

Figure 5:
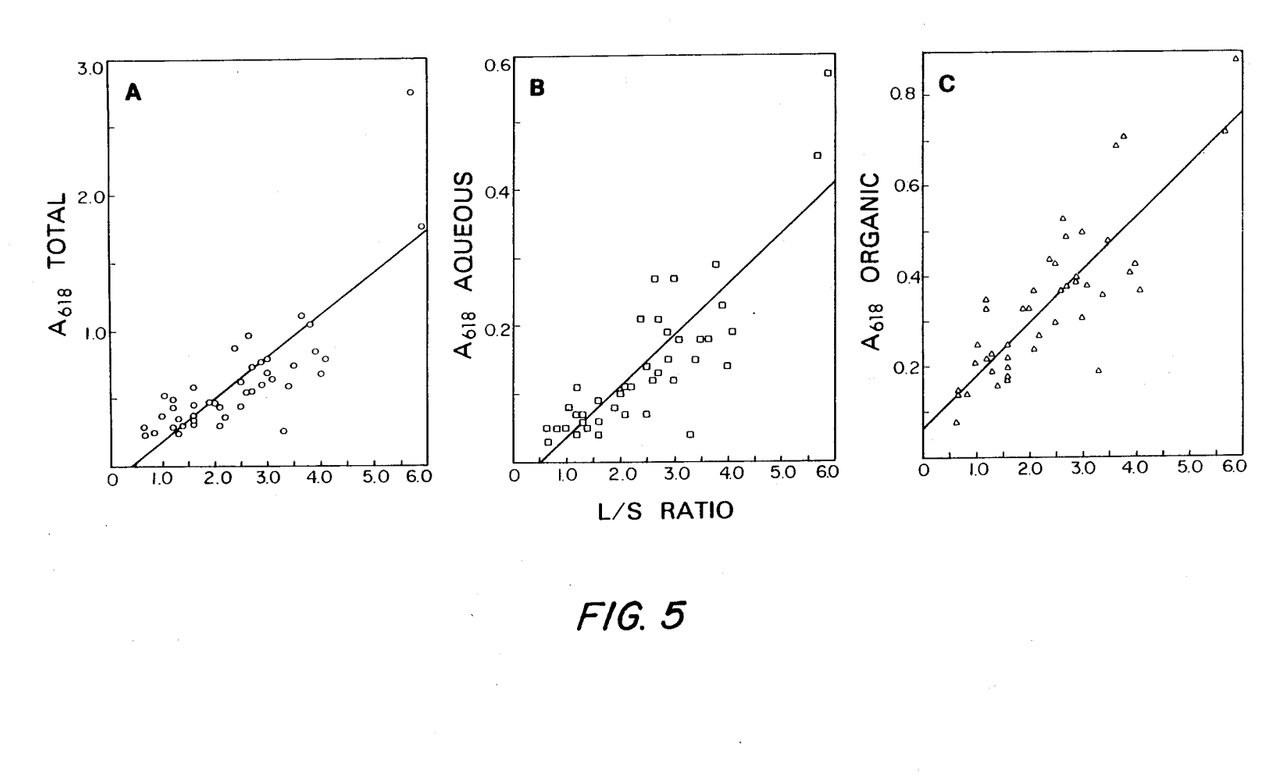

Finally, there is an excellent agreement between values obtained by the inventive assay and L/S ratios of amniotic fluid from uncomplicated pregnancies. This is shown in FIG. 5 where values obtained with the inventive assay were plotted against L/S ratios. The linear lines were calculated by a least square regression analysis. The correlation coefficient prior to organic solvent extraction of the blue solution resulting from the application of the inventive assay to the samples was 80%. After the extraction, the aqueous and the organic phases gave a correlation coefficient of 84% with the L/S ratio.

The absorbance of the phospholipid-dye-detergent solution, resulting from solubilization of a dye-detergent complex obtained by filtration or centrifugation, could also be resolved by chloroform-methanol extraction into components of charged and uncharged phospholipids. Sensitivity can be enhanced by adding ammonium sulfate to 1% saturation to the phospholipid dye-detergent solution before the chloroform-methanol extraction. The mixture is then centrifuged (10,000×g, 10 min) and the resultant dye complex pellet is resuspended in the desired volume of methanol.

The dye-detergent complex may also be formed using other combinations of dyes and detergents. The negatively charged dye congo red and CTAB, as well as the positively charged dyes of methyl violet and malachite green and negatively charged detergent SDS may also be used.

In conclusion, the instant assay can determine rapidly the total concentration of charged, uncharged and total phospholipids in amniotic fluid. When specific determination of certain lipids, for example, PG or PI are needed, these lipids can be separated on a microcolumn of silica gel and then be determined by the assay in individual fractions.

TABLE I

| SOLUBILIZATION of DYE-DETERGENT COMPLEX by PHOSPHOLIPID LIPOSOMES | | |
|---|---|---|
| Phospholipid concentration (μg/ml) | Phospholipid | Absorbance[2] at 618 nm |
| 5 | PG | 0.14 |
| 5 | PC | 0.07 |
| 10 | PG | 0.27 |
| 10 | PC | 0.11 |
| 25 | PG | 0.50 |
| 25 | PC | 0.21 |
| 50 | PG | 0.92 |
| 50 | PC | 0.18 |

[1]A. 1.0 ml liposome sample was incubated with CBB-CTAB complex, as prepared in Method 2a. The absorbance at 618 nm is given as a function of phospholipid concentration.
[2]The changes in absorbance after subtraction of water-control values are given.

TABLE II

| BIPHASIC EXTRACTION OF ASSAY PRODUCTS[1] | | | |
|---|---|---|---|
| Lipids (μg/ml) | $A_{618}$[2] | $A_{618}$ (aq)[3] | $A_{618}$ (org)[4] |
| 2 PG | 0.06 | 0.05 | 0.02 |
| 5 PG | 0.13 | 0.10 | 0.02 |
| 15 PI | 0.25 | 0.20 | 0.05 |
| 10 PC | 0.16 | 0.02 | 0.12 |
| 25 PC | 0.29 | 0.02 | 0.22 |
| 10 S | 0.043 | 0.01 | 0.03 |
| 20 PE | 0.23 | 0.01 | 0.18 |
| 5 PG + 25 PC | 0.40 | 0.10 | 0.24 |

[1]Dye-detergent complex (10 beads) was solubilized by 2.0 ml of the indicated lipid solution and was extracted with 3 ml of chloroform and 2 ml of methanol.
[2]Absorbance at 618 nm, after subtraction of controls, of 2 ml of assay products before extraction.
[3]The absorbance of the aqueous phase at 618 nm after chloroform-methanol extraction. A factor of 1.5, which was determined experimentally, was used to compensate for changes in volume of the lipid-dye-detergent solution and different extinction coefficient of the product in 1:1 v/v of water to methanol.
[4]Absorbance at 618 nm of the organic phase. No corrections were made for change in volume or possible different extinction coefficient from products in the second column.

TABLE III

ASSAY FOR MIXTURES OF PHOSPHOLIPIDS

| Lipids (μg/ml)[1] | $A_{618}$ (aq)[2] | $A_{618}$ (org)[2] |
|---|---|---|
| 2 PG | 0.04 | 0.01 |
| 25 PC | 0.02 | 0.26 |
| 2 PG + 25 PC | 0.05 | 0.21 |

[1]Several assays were averaged. Each assay consisted of 2 ml liposomes and 10 complex-coated beads.
[2]Assays performed with $H_2O$, gave values of 0.03 and 0.07 in aqueous and chloroform, respectively, and were subtracted as controls.

TABLE IV

ASSAY FOR MIXTURES OF PHOSPHOLIPIDS IN AMNIOTIC FLUID

| Amniotic fluid[1] added phospholipid(μg/ml) | $A_{618}$ (aq)[2] | $A_{618}$ (org)[2] |
|---|---|---|
| 2.5 PG | 0.05 | 0.00 |
| 8 PI | 0.08 | 0.00 |
| 2.5 PG + 20.0 PC | 0.05 | 0.12 |

[1]Amniotic fluids with L/S ratios >2 were pooled and 2 ml aliquots extracted by the chloroform-methanol method (4). Exogenous lipids were added to the chloroform phase and dried under nitrogen.
[2]Assays performed with amniotic fluid gave values of 0.11 and 0.61 in aqueous and chloroform, respectively, and were subtracted as controls.

It will be appreciated that the present invention is not limited to application within the field of predicting Respiratory Distress Syndrome in newborns, but finds ready application in various other types of testing wherein a determination of lipid content of a sample is required.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

What is claimed is:

1. An enzyme-free, non-hydrolyzing assay useful for determination of lipid content of a lipid-containing fluid which comprises forming a water insoluble complex of a charged dye and an oppositely charged detergent, incubating the dye-detergent complex in an aqueous dispersion of a lipid-containing fluid thereby imparting a characteristic color to the lipid containing fluid, said characteristic color exhibiting light absorbance, and measuring the light absorbance of the characteristic color whereby the lipid content of the fluid is determined.

2. The assay of claim 1 wherein the dye in the dye-detergent complex is Coomassie Brilliant Blue.

3. The assay of claim 1 wherein the detergent in the dye-detergent complex is cetyltrimethylammoniumbromide.

4. The assay of claim 1 wherein the dye in the dye-detergent complex is Coomassie Brilliant Blue an the detergent in the dye-detergent complex is cetyltrimethylammoniumbromide.

5. An enzyme-free, non-hydrolyzing assay useful for determination of lipid content of a lipid-containing fluid, which comprises formation of a dye-detergent complex of a charged dye and an oppositely charged detergent,
incubation of the dye-detergent complex in an aqueous dispersion of lipid containing fluid to form a dye-detergent-lipid colored solution which colored solution exhibits light absorbance, and
measurement of the light absorbance of the dye-detergent-lipid colored solution thereby determining the lipid content of the fluid.

6. The assay of claim 5 wherein the dye-detergent complex is absorbed onto glass beads prior to incubation in the aqueous dispersion of lipid containing fluid.

7. The assay of claim 5 wherein the dye-detergent complex is deposited onto a filter prior to incubation of the dye-detergent complex in an aqueous dispersion of lipid containing fluid.

8. An enzyme-free, non-hydrolyzing assay useful for evaluation of respective concentrations of anionic and zwitterionic lipids and total lipid content of a lipid-containing fluid, which comprises forming a dye-detergent complex of a charged dye and an oppositely charged detergent which complex when deposited onto support strata will interact with said support strata,
incubating the dye-detergent complex in an aqueous dispersion of lipid-containing fluid to form a dye-detergent-lipid colored solution,
separating the dye-detergent-lipid colored solution into a colored aqueous phase and a colored organic phase, each phase exhibiting light absorbance, and
measuring the respective light absorbance of the aqueous and organic phases to determine the respective concentrations of anionic and zwitterionic lipids and the total lipid content of the fluid sample.

9. An enzyme-free, non-hydrolyzing assay useful for evaluation of respective concentrations of anionic and zwitterionic phospholipids and total phospholipid content of a phospholipid-containing fluid, which comprises forming a dye-detergent complex of a charged dye and an oppositely charged detergent, which complex when deposited onto support strata will interact with said support strata,
incubating the dye-detergent complex in an aqueous dispersion of phospholipid-containing fluid to form a dye-detergent-phospholipid colored solution,
separating the dye-detergent-phospholipid colored solution into a colored aqueous phase and a colored organic phase each phase exhibiting light absorbance, and
measuring the respective light absorbance of the aqueous and organic phases to determine the respective concentrations of anionic and zwitterionic phospholipids and the total phospholipid content of the fluid sample.

10. A method of predicting Respiratory Distress Syndrome through measurement of respective concentrations of anionic and zwitterionic lipids and total lipid content in amniotic fluid, which comprises forming a dye-detergent complex of a charged dye and an oppositely charged detergent which complex when deposited onto support strata will interact with said support strata,
incubating the dye-detergent complex with an aqueous dispersion of lipids extracted from amniotic fluid to form a dye-detergent-lipid colored solution,
separating the dye-detergent-lipid colored solution into a colored aqueous phase and a colored organic phase each phase exhibiting light absorbance,
measuring the respective light absorbance of the colored aqueous and colored organic phases thereby determining the respective concentrations of anionic and zwitterionic lipids and the total lipid content in the amniotic fluid, and evaluating the respective concentrations of anionic and zwitterionic lipids and total lipid content in the amniotic fluid, thereby enabling the prediction of Respiratory Distress Syndrome.

11. A method for the evaluation of fetal pulmonary maturity which comprises forming a dye-detergent complex of a charged dye and an oppositely charged detergent which complex when deposited onto support strata will interact with said support strata, incubating the dye-detergent complex with an aqueous dispersion of lipids extracted from amniotic fluid to form a dye-detergent-lipid colored solution, separating the dye-detergent-lipid colored solution into a colored aqueous phase and colored organic phase each phase exhibiting light absorbance, and measuring the respective light absorbance of the colored aqueous and colored organic phases thereby determining the respective concentrations of anionic and zwitterionic lipids and the total lipid content in the amniotic fluid, evaluating the respective concentrations of anionic and zwitterionic lipids and total lipid content in the amniotic fluid thereby providing an evaluation of fetal pulmonary maturity.

* * * * *